United States Patent
Blanda et al.

(10) Patent No.: US 9,050,336 B2
(45) Date of Patent: *Jun. 9, 2015

(54) BOTULINUM TOXIN FORMULATION

(75) Inventors: Wendy M. Blanda, Tustin, CA (US);
Roger K. Aoki, Coto de Caza, CA (US);
Terrence J. Hunt, Corona, CA (US);
Patrick M. Hughes, Aliso Viejo, CA (US); James N. Chang, Newport Beach, CA (US); Scott M. Whitcup, Laguna Hills, CA (US); Michael R. Robinson, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 364 days.

This patent is subject to a terminal disclaimer.

(21) Appl. No.: 13/466,806

(22) Filed: May 8, 2012

(65) Prior Publication Data
US 2014/0302007 A1    Oct. 9, 2014

Related U.S. Application Data

(63) Continuation of application No. 11/954,629, filed on Dec. 12, 2007.

(51) Int. Cl.
| | | |
|---|---|---|
| *A61K 38/00* | (2006.01) | |
| *A61K 31/728* | (2006.01) | |
| *A61K 39/00* | (2006.01) | |
| *A61K 38/48* | (2006.01) | |
| *A61K 9/00* | (2006.01) | |
| *A61K 47/36* | (2006.01) | |

(52) U.S. Cl.
CPC ..... *A61K 38/4893* (2013.01); *C12Y 304/24069* (2013.01); *A61K 9/0024* (2013.01); *A61K 47/36* (2013.01); *A61K 9/0019* (2013.01)

(58) Field of Classification Search
CPC ... A61K 39/08; A61K 2300/00; A61K 38/07; A61K 38/4893; A61K 31/728; A61K 39/00
USPC .......................................... 424/239.1; 514/1.1
See application file for complete search history.

(56) References Cited

U.S. PATENT DOCUMENTS

| | | | |
|---|---|---|---|
| 4,636,524 A | 1/1987 | Balazs et al. | |
| 4,713,448 A | 12/1987 | Balazs et al. | |

(Continued)

FOREIGN PATENT DOCUMENTS

| | | | |
|---|---|---|---|
| WO | WO/97/49412 | | 12/1997 |
| WO | WO2004/060384 | * | 7/2004 |
| WO | WO 2006/020208 A2 | | 2/2006 |

OTHER PUBLICATIONS

Aoki et al. Using translational medicine to understand clinical differences between Botulinum Toxin formulation. E. J. of Neuro12006. 13 (Suppl. 4) 10-19.

(Continued)

*Primary Examiner* — Albert Navarro
*Assistant Examiner* — Ginny Portner
(74) *Attorney, Agent, or Firm* — Brigitte C. Phan; Ted A. Chan; Debra D. Condino

(57) ABSTRACT

*Botulinum* neurotoxin formulated with a hyaluronic acid carrier with increased residency time of the *botulinum* toxin at a subdermal location and fewer *botulinum* toxin induced complications or side effects.

7 Claims, 2 Drawing Sheets
(1 of 2 Drawing Sheet(s) Filed in Color)

(56) References Cited

U.S. PATENT DOCUMENTS

| | | | | |
|---|---|---|---|---|
| 5,099,013 | A | 3/1992 | Balazs et al. | |
| 5,143,724 | A | 9/1992 | Leshchiner et al. | |
| 5,512,547 | A * | 4/1996 | Johnson et al. | 514/15.2 |
| 5,756,468 | A * | 5/1998 | Johnson et al. | 424/780 |
| 6,306,423 | B1 * | 10/2001 | Donovan et al. | 424/423 |
| 6,312,708 | B1 * | 11/2001 | Donovan | 424/423 |
| 6,506,399 | B2 * | 1/2003 | Donovan | 424/423 |
| 7,277,537 | B2 * | 10/2007 | Li | 379/386 |
| 7,465,458 | B2 * | 12/2008 | First | 424/247.1 |
| 7,491,403 | B2 * | 2/2009 | Borodic | 424/239.1 |
| 7,579,010 | B2 * | 8/2009 | Hunt | 424/236.1 |
| 7,691,394 | B2 * | 4/2010 | Borodic | 424/239.1 |
| 7,727,537 | B2 * | 6/2010 | Modi | 424/239.1 |
| 7,758,873 | B2 * | 7/2010 | Hunt | 424/247.1 |
| 7,780,635 | B2 * | 8/2010 | Pruitt et al. | 604/187 |
| 7,838,011 | B2 * | 11/2010 | Modi | 424/239.1 |
| 8,168,206 | B1 * | 5/2012 | Hunt | 424/247.1 |
| 8,206,335 | B2 * | 6/2012 | Pruitt et al. | 604/19 |
| 8,318,181 | B2 * | 11/2012 | Edelson et al. | 424/239.1 |
| 8,323,666 | B2 * | 12/2012 | Hunt | 424/239.1 |
| 8,399,007 | B2 * | 3/2013 | Taft et al. | 424/423 |
| 8,486,467 | B1 * | 7/2013 | Prescott | 424/780 |
| 8,518,414 | B2 * | 8/2013 | Waugh | 424/239.1 |
| 8,557,255 | B2 * | 10/2013 | Marx et al. | 424/239.1 |
| 8,580,250 | B2 * | 11/2013 | Hunt | 424/94.3 |
| 8,580,290 | B2 * | 11/2013 | DeAngelis | 424/423 |
| 8,586,020 | B2 * | 11/2013 | Song et al. | 424/78.17 |
| 8,632,785 | B2 * | 1/2014 | Hunt | 424/247.1 |
| 8,647,639 | B2 * | 2/2014 | First | 424/234.1 |
| 8,691,279 | B2 * | 4/2014 | Guillen et al. | 424/488 |
| 8,801,659 | B2 * | 8/2014 | Mudd et al. | 604/85 |
| 2002/0028216 | A1 | 3/2002 | Donovan | 424/236.1 |
| 2002/0086036 | A1 * | 7/2002 | Walker | 424/236.1 |
| 2003/0068365 | A1 * | 4/2003 | Suvanprakorn et al. | 424/450 |
| 2003/0118598 | A1 * | 6/2003 | Hunt | 424/184.1 |
| 2004/0033241 | A1 * | 2/2004 | Donovan | 424/239.1 |
| 2004/0086531 | A1 * | 5/2004 | Barron | 424/239.1 |
| 2004/0086532 | A1 * | 5/2004 | Donovan | 424/239.1 |
| 2004/0170665 | A1 * | 9/2004 | Donovan | 424/427 |
| 2004/0234532 | A1 * | 11/2004 | First | 424/184.1 |
| 2005/0101582 | A1 | 5/2005 | Lyons et al. | |
| 2005/0143289 | A1 * | 6/2005 | Hunt | 514/2 |
| 2005/0181017 | A1 | 8/2005 | Hughes et al. | |
| 2005/0214327 | A1 * | 9/2005 | Brooks et al. | 424/239.1 |
| 2005/0238664 | A1 * | 10/2005 | Hunt | 424/239.1 |
| 2005/0244258 | A1 * | 11/2005 | Weiland | 414/539 |
| 2005/0250737 | A1 | 11/2005 | Hughes et al. | |
| 2005/0281861 | A1 | 12/2005 | Hughes et al. | |
| 2006/0018931 | A1 * | 1/2006 | Taylor | 424/239.1 |
| 2006/0040894 | A1 * | 2/2006 | Hunter et al. | 514/54 |
| 2006/0062768 | A1 * | 3/2006 | Hnojewyj | 424/93.7 |
| 2006/0093624 | A1 * | 5/2006 | Graham | 424/239.1 |
| 2006/0115457 | A1 * | 6/2006 | Hnojewyj | 424/93.7 |
| 2006/0141049 | A1 | 6/2006 | Lyons et al. | |
| 2006/0161253 | A1 * | 7/2006 | Lesh | 623/8 |
| 2006/0182794 | A1 * | 8/2006 | Modi | 424/450 |
| 2006/0269575 | A1 * | 11/2006 | Hunt | 424/239.1 |
| 2006/0286127 | A1 * | 12/2006 | Van Schaack et al. | 424/239.1 |
| 2007/0178121 | A1 * | 8/2007 | First et al. | 424/239.1 |
| 2007/0179117 | A1 * | 8/2007 | Reiner et al. | 514/54 |
| 2007/0224278 | A1 | 9/2007 | Lyons et al. | |
| 2007/0269463 | A1 * | 11/2007 | Donovan | 424/239.1 |
| 2007/0286881 | A1 * | 12/2007 | Burkinshsw | 424/422 |
| 2008/0044476 | A1 * | 2/2008 | Lyons et al. | 424/488 |
| 2008/0241252 | A1 | 10/2008 | Lyons et al. | |
| 2008/0268051 | A1 | 10/2008 | Hughes et al. | |
| 2008/0274946 | A1 * | 11/2008 | Giampapa | 514/3 |
| 2009/0010884 | A1 * | 1/2009 | Chang et al. | 424/85.5 |
| 2009/0082321 | A1 * | 3/2009 | Edelman et al. | 514/178 |
| 2010/0136070 | A1 * | 6/2010 | Dobak et al. | 424/401 |
| 2010/0160849 | A1 * | 6/2010 | Barbour | 604/20 |
| 2010/0172940 | A1 * | 7/2010 | Petrella | 424/239.1 |
| 2010/0280488 | A1 * | 11/2010 | Pruitt et al. | 604/506 |
| 2011/0077229 | A1 * | 3/2011 | Edelman et al. | 514/180 |
| 2011/0135742 | A1 * | 6/2011 | Kim et al. | 424/499 |
| 2012/0082717 | A1 * | 4/2012 | Char et al. | 424/450 |
| 2012/0093866 | A1 * | 4/2012 | Burger et al. | 424/239.1 |
| 2012/0238504 | A1 * | 9/2012 | Moyer et al. | 514/18.1 |
| 2012/0283656 | A1 * | 11/2012 | Pruitt et al. | 604/211 |
| 2013/0251786 | A1 * | 9/2013 | Li et al. | 424/450 |
| 2014/0105884 | A1 * | 4/2014 | Konorty et al. | 424/94.67 |

OTHER PUBLICATIONS

Aoki, Roger K. Botulinum neurotoxin serotypes A and B preparations have diff. safety margins in preclinical models of muscle weakening efficacy and systemic safety. Toxicon 40 (2002) 923-928.

Aoki, Roger K. A comparison of the safety margins of Botulinum neurotoxin serotypes A, B, and F in mice. Toxicon 39 (2001) 1815-1820.

Armstrong et al. Relationship between lymph and tissue hyaluronan in skin and skeletal muscle. Am J of physiol 2002, H2485-H2494.

Brandt et al. Hyaluronic Acid Fillers. Restylane and Perlane. Facial Plastic surgery Clinics of N.A. Elsevier 2006.

Brin, Mitchell F. The pharmacology of Botulinum Toxin, Muscle & Nerve Suppl 6,1997.

Carruthers et al (2003 Dermatologic Surgery vol. 29 pp. 802-809).

Carruthers, J. et al. Complication of Botulinum Toxin Type A. Elsevier Saunders 2006, pp. 51-54.

Foster Keith A. et al. Botulinum Neurotoxin—From Laboratory to Bedside. Neuro Res 2006, vol. 9(2,3). pp. 133-140.

Francis J. et al. Pharmacological Evaluation of BOTOX®, Dysport® and MyobloC® in models of efficacy and safety.

Harrison's Principles of Internal Medicine (1998), edited by Anthony Fauci et al., 14th edition, published by McGraw Hill).

McCourt Peter A. G. How does the hyaluronan scrap-yard operate. Matrix Biology 18 (1999) 427-432.

Noble Paul W. Hyaluronan and its catabolic products in tissue injury and repair. Matrix Biology 21 (2002) 25-29.

Prodanov D et al. Three-Dimensional Topography of the Motor Endplates of the Rat Gastrocnemius Muscle. Muscle Nerve Sep. 2005.

Simpson Lance L. The Origin, Structure, and Pharmacological Activity of Botulinum Toxin. Phamacol Rev 1981; 33(3): 155-88.

Tognana E. et al. Hyalograft® C: Hyaluronan-Based Scaffolds in Tissue-Engineered Cartilage. Cells Tissue Organs 2007; 186:97-103.

* cited by examiner

BOTULINUM TOXIN FORMULATION

RELATED APPLICATION

This application is a continuation of U.S. application Ser. No. 11/954,629, filed Dec. 12, 2007, which is incorporated herein in its entirety.

BACKGROUND

The present invention relates to an improved *botulinum* toxin formulation. In particular the present invention relates to an injectable *botulinum* toxin-hyaluronic acid formulation which can be administered with reduced local and systemic *botulinum* toxin induced complications.

A pharmaceutical composition (synonymously a formulation or a composition) is a formulation which contains at least one active ingredient (for example a *botulinum* neurotoxin) as well as, for example, one or more excipients, buffers, carriers, stabilizers, preservatives and/or bulking agents, and is suitable for administration to a human patient to achieve a desired effect or result. The pharmaceutical compositions disclosed herein can have diagnostic, therapeutic, cosmetic and/or research utility.

Hyaluronic Acid

Hyaluronic acid (also called hyaluronan or sodium hyaluronate) is a naturally occurring polysaccharide found in joints, connective tissue and the eye. Hyaluronic acid is a glycosaminoglycan (a mucopolysaccharide) which is a long unbranched polysaccharide composed of repeating dimeric units of glucuronic acid and N acetyl glucosamine. U.S. Pat. Nos. 4,636,524; 4,713,448; 5,099,013, and 5,143,724 disclose particular hyaluronic acids and methods for making them.

Hyaluronic acid has known therapeutic and cosmetic uses. For example, intra-articular use of hyaluronic acid as a viscosupplement to treat osteoarthritis joint pain is known (eg ORTHOVISC® (Anika), DUROLANE® (Smith & Nephew), HYALGAN® (Sanofi), HYLASTAN® (Genzyme), SUPARTZ® (Seikagaku/Smith & Nephew), SYNVISC® (Genzyme), and EUFLEXXA®, (Ferring). Hyaluronic acid is also used cosmetically as an injectable dermal filler (eg JUVEDERM™ (Allergan).

U.S. patent applications which disclose use of therapeutic agent formulated with a hyaluronic acid include application Ser. No. 10/966,764, filed Oct. 14, 2004, application Ser. No. 11/091,977, filed Mar. 28, 2005, application Ser. No. 11/354,415, Feb. 14, 2006, application Ser. No. 11/741,366, filed Apr. 27, 2007, application Ser. No. 11/828,561, filed Jul. 26, 2007, application Ser. No. 11/039,192, filed Jan. 19, 2005, application Ser. No. 11/116,698, filed Apr. 27, 2005, application Ser. No. 11/695,527, filed Apr. 2, 2007, and application Ser. No. 11/742,350, filed Apr. 30, 2007.

Botulinum Toxin

The anaerobic, gram positive bacterium *Clostridium botulinum* produces a potent polypeptide neurotoxin called *botulinum* neurotoxin toxin which causes a neuroparalytic illness in humans and animals referred to as botulism. *Botulinum* toxin type A is the most lethal natural biological agent known to man. About 50 picograms of a commercially available *botulinum* toxin type A (purified neurotoxin complex)[1] is a $LD_{50}$ in mice (i.e. 1 unit). One unit of BOTOX® contains about 50 picograms (about 56 attomoles) of *botulinum* toxin type A complex. One unit (U) of *botulinum* toxin is defined as the $LD_{50}$ upon intraperitoneal injection into female Swiss Webster mice weighing 18 to 20 grams each.

Seven, generally immunologically distinct *botulinum* neurotoxins have been characterized, these being respectively *botulinum* neurotoxin serotypes A, B, $C_1$, D, E, F and G each of which is distinguished by neutralization with type-specific antibodies. The different serotypes of *botulinum* toxin vary in the animal species that they affect and in the severity and duration of the paralysis they evoke. *Botulinum* toxin apparently binds with high affinity to cholinergic motor neurons, is translocated into the neuron and blocks the release of acetylcholine.

*Botulinum* toxins have been used for the treatment of various therapeutic and cosmetic conditions. A *botulinum* toxin type A (Allergan, Inc., BOTOX®) has been approved by the U.S. Food and Drug Administration for the treatment of blepharospasm, strabismus, cervical dystonia, hyperhydrosis and glabellar lines.

The molecular weight of the neurotoxic component of a *botulinum* toxin complex is about 150 kD. *Botulinum* toxin is typically made by the Clostridial *botulinum* bacterium as a complex comprising the 150 kD *botulinum* toxin protein molecule and associated non-toxin proteins. Thus, a *botulinum* toxin type A complex can be produced by Clostridial bacterium as 900 kD, 500 kD and 300 kD complex forms.

A commercially available *botulinum* toxin containing pharmaceutical composition is sold under the trademark BOTOX® (available from Allergan, Inc., of Irvine, Calif.). BOTOX® consists of a purified *botulinum* toxin type A complex, albumin and sodium chloride packaged in sterile, vacuum-dried form. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative. Other commercially available *botulinum* neurotoxins approved for use in humans include DYSPORT® (Beaufour Ipsen, Porton Down, England) XEOMIN® (Merz Pharmaceuticals GmbH, Frankfurt, Germany) and MYOBLOC® (Solstice Neurosciences, San Francisco, Calif.).

Botulinum Toxin Complications

Local and systemic complications can occur when a *botulinum* neurotoxin is administered (as by injection) into a muscle or a subcutaneous tissue for a therapeutic or cosmetic purpose. Complications subsequent to injection of a *botulinum* neurotoxin for a therapeutic or cosmetic purpose can be due to diffusion of the *botulinum* neurotoxin from the site of injection into adjacent muscle groups. Examples of known local complications upon injection of a *botulinum* toxin to treat blepharospasm, strabismus and cervical dystonia follow.

Blepharospasm (uncontrolled blinking) is characterized by involuntary, intermittent, forced eyelid closure. *Botulinum* toxin has been used to treat various types of blepharospasm, including blepharospasm induced by drugs such as L-dopa or neuroleptics, dystonic eyelid and facial tics in patients with Tourette syndrome, and apraxia of eyelid opening. Treatment of essential blepharospasm with a *botulinum* toxin requires injection of the neurotoxin into the orbicularis muscle. Unfortunately, the *botulinum* neurotoxin can diffuse out of this muscle into the deeper levator muscle resulting in ptosis and visual field impairment that can persist for several weeks to months. Additionally, brow ptosis can also occur with deeper diffusion of the *botulinum* neurotoxin out of the orbicularis muscle into the frontalis muscle. Although the medial aspect of the lower lid does not receive an injection, the *botulinum* toxin can diffuse into this area leading to a medial ectropion and chronic tearing. Patients can also experience double vision if the *botulinum* neurotoxin diffuses into the deeper rectus muscles. Uncommonly, unintended diffusion of the botulinum toxin into the zygomaticus major muscle occurs which can lead to an asymmetric facial expression.

Strabismus (crossed eyes) can be treated by injecting a botulinum toxin into individual rectus muscles. For example, the medial rectus muscles can be injected with a botulinum toxin under EMG guidance for treating esotropia. Local inadvertent diffusion of the botulinum toxin into the muscle cone can lead to paralysis of other recti leading to double vision and inadequate correction of the esotropia.

Cervical dystonia is the most common form of focal dystonia and is characterized by sustained abnormal postures or contractions of the neck muscles. Deviation of the head can occur in multiple directions; turning of head (torticollis) is the most common subtype of cervical dystonia. Treatment of cervical dystonia with a botulinum toxin can improve the patient's posture and function and to relieve associated pain. Although the intent of botulinum toxin treatment is to inject into selected muscle group, for example the sternocleidomastoid muscle, occasionally under EMG guidance, local diffusion of the botulinum toxin out of the muscle area may occur causing unintentional paralysis of adjacent muscles. Diffusion of the botulinum neurotoxin into the deep neck muscles can cause weakness of the pharyngeal and esophageal muscles and resultant difficulty with swallowing (dysphagia) occasionally is severe enough to require a modified diet and monitoring for aspiration. Dysarthria, difficulty with speech, can also occur. Dysphagia is a commonly reported adverse event following treatment of cervical dystonia patients with a botulinum toxin. In these patients, there are reports of rare cases of dysphagia severe enough to warrant the insertion of a gastric feeding tube. Aspiration pneumonia and death from dysphagia has also occurred after botulinum toxin administration.

Systemic complications upon local intramuscular injection of a botulinum toxin have also been reported. Thus, respiratory distress following an intramuscular botulinum toxin injection can occur from excessive systemic absorption and paralysis of the diaphragm. A number of cases of systemic botulism-like reaction with generalized weakness including bulbar weakness resolved over several weeks has been reported.

Preclinical studies have demonstrated differences in local vs systemic effects of different commercially available botulinum toxin products. Systemic effects may be due to escape of the intramuscularly administered botulinum toxin into the circulation.

What is therefore needed is a botulinum toxin formulation of which the botulinum toxin therein shows a reduced tendency to diffuse from the site of administration upon local (i.e. intramuscular or subcutaneous) injection of the botulinum toxin formulations, thereby reducing complications and side effects upon botulinum toxin administration for a therapeutic or cosmetic purpose.

SUMMARY

The present invention meets this need and provides a botulinum toxin formulated with a polymeric carrier. The formulation is injected as a depot and shows reduced diffusion of the botulinum toxin from the injection thereby reducing potential local and systemic botulinum toxin induced complications or side effects.

Definitions

As used herein, the words or terms set forth below have the following definitions.

"About" means that the item, parameter or term so qualified encompasses a range of plus or minus ten percent above and below the value of the stated item, parameter or term.

"Administration" or "to administer" means the step of giving (i.e. administering) a pharmaceutical composition to a subject. The pharmaceutical compositions disclosed herein are "locally administered" (local administration), that is administered at or in the vicinity of the site at which a therapeutic result or outcome is desired. For example to treat an peripheral condition by peripheral administration of a viscous formulation. Sustained release" means release of an active agent (such as a botulinum neurotoxin) over a period of about seven days or more, while "extended release" means release of an active agent over a period of time of less than about seven days.

"Botulinum toxin" means a botulinum neurotoxin type A, B, C, D, E, F or G as either pure toxin (i.e. the about 150 kiloDalton molecular weight neurotoxic component) or as a botulinum toxin complex (about 300 to about 900 kiloDaltons molecular weight), including recombinant, chimeric, hybrid, retargeted, and amino acid sequence modified botulinum neurotoxins, but excluding botulinum toxins which are not neurotoxins such as the cytotoxic botulinum toxins $C_2$ and $C_3$.

"Entirely free (i.e. "consisting of" terminology) means that within the detection range of the instrument or process being used, the substance cannot be detected or its presence cannot be confirmed, or that the condition, complication or side effect does not exist. "Essentially free" (or "consisting essentially of") means that only trace amounts of the substance can be detected, or that the condition, complication or side effect is experienced by a patient for less than 10% to 20% of the time.

"Local administration" means administration (i.e. by a subcutaneous, intramuscular, subdermal, intradermal, subcutaneous, intra-organ [eg injected into the bladder wall or into the body of the prostate] or transdermal route) of a pharmaceutical agent to or to the vicinity of a target tissue, muscle or subdermal location by a non-systemic route. Thus, local administration excludes systemic (i.e. to the blood circulation system) routes of administration, such as intravenous or oral administration. Peripheral administration means administration to the periphery (i.e. to a location on or within a face, limb, trunk or head of a patient) as opposed to a visceral or gut (i.e. to the viscera) administration.

"Pharmaceutical composition" means a formulation in which an active ingredient (the active agent) can be a botulinum neurotoxin. The word "formulation" means that there is at least one additional ingredient in the pharmaceutical composition besides the active agent. A pharmaceutical composition is therefore a formulation which is suitable for diagnostic or therapeutic administration (i.e. by subdermal or intramuscular injection) to a subject, such as a human patient.

"Substantially free" means present at a level of less than one percent by weight of the pharmaceutical composition, or that the condition, complication or side effect is experienced by a patient less than 50% of the time.

"Sustained release" means release of an active agent (such as a triamcinolone) over a period of about seven days or more, while "extended release" means release of an active agent over a period of time of less than about seven days.

"Viscous carrier" means a biocompatible compound which when formulated with a botulinum neurotoxin provides upon in vivo local injection of the formulation a depot from which the botulinum toxin is released in amounts such that the extent of diffusion of the botulinum toxin away from the site of the local injection and/or the amount of the botulinum toxin which diffuses away from the site of local injection is significantly reduced as evidenced by a substantial reduction of *botulinum* toxin complications, as compared to the incidence of *botulinum* toxin complications which occur upon injection of a *botulinum* toxin (such as BOTOX®, DYSPORT®, XEOMIN® and MYOBLOC®) which does not comprise a viscous carrier.

All the viscosity values set forth herein were determined at 25° C. (unless another temperature is specified). Additionally, all the viscosity values set forth herein were determined at a shear rate of about 0.1/second (unless another shear rate is specified).

Our invention is a pharmaceutical composition comprising a *botulinum* neurotoxin and a viscous carrier for the *botulinum* neurotoxin. The viscous carrier can be selected from the group of viscous carriers consisting of hyaluronic acid, carbomer, polyacrylic acid, cellulose polycarbophil, polyvinylpyrrolidone, gelatin, dextrin, polysaccharide, polyacrylamide, polyvinyl alcohol, polyvinyl acetate, chitosans, algenates and derivatives and mixtures thereof. Preferably, the viscous carrier is a hyaluronic acid, such as a non-cross linked hyaluronic acid or a cross linked hyaluronic acid. The hyaluronic acid can be a polymeric hyaluronic acid with a molecular weight between about 10,000 Daltons and about 20 million Daltons. The concentration of the hyaluronic acid in the formulation (in the pharmaceutical composition) can be between about 1 wt % and about 10 wt %, such as between about 0.1 wt % and about 1 wt %.

The pharmaceutical composition can have a viscosity of between about 1000 cps and about 300,000 cps at 25° C., at a shear rate of 0.1/second or between about 100 cps and about 1,000 cps at 25° C., at a shear rate of 0.1/second.

A detailed embodiment of our invention is a pharmaceutical composition comprising a *botulinum* neurotoxin and a cross linked, polymeric, hyaluronic acid carrier for the *botulinum* neurotoxin, wherein the polymeric hyaluronic acid has a molecular weight between about 10,000 Daltons and about 20 million Daltons, the concentration of the polymeric hyaluronic acid in the formulation is between about 0.1 wt % and about 1 wt % and the viscosity of the pharmaceutical composition is between about 100 cps and about 1,000 cps at 25° C., at a shear rate of about 0.1/second. The *botulinum* neurotoxin is preferably a *botulinum* neurotoxin type A.

Our invention also encompasses a method for treating a disease or condition in a human patient by administering to the patient a pharmaceutical composition comprising a *botulinum* neurotoxin and a viscous carrier for the *botulinum* neurotoxin, wherein the patient experiences significantly fewer complications due to the *botulinum* toxin than occur upon administration of a *botulinum* toxin formulation which does not comprise a viscous carrier. The administering can be carried out by local subdermal injection of the pharmaceutical composition. The disease or condition treated can be, for example, a dystonia (such as cervical dystonia), blepharospasm, strabismus, spasticity, movement disorder, headache, migraine, hyperhydrosis, overactive bladder, prostate disorder, articular pathology, arthritis, facial wrinkles, and glabellar lines. The complications experienced at a lower incidence can be local complications such as ptosis, brow ptosis, visual field impairment, double vision, ectropion, tearing, asymmetric facial expression, dysphagia, and muscle weakness, or systemic complications selected from the group of system complications consisting of respiratory distress, generalized weakness, dry mouth, nausea, headache, constipation and vertigo. Importantly, the patient can experiences no complications during any ten day period up to six months after the administration. Furthermore, the patient can experience during any ten day period up to six months after the administration a complication which persists, as reported by the patient, for only 10% to 50% of the period of time the same complication is experienced by the patient upon administration of a *botulinum* toxin formulation which is injected into the patient at the same location, to treat the same disease or condition, and which contains the same amount of the *botulinum* toxin, but which does not comprise a viscous carrier acid.

Our invention also includes a process for making a pharmaceutical composition, the process comprising the steps of preparing a pharmaceutical composition comprising a *botulinum* neurotoxin and a viscous carrier for the *botulinum* neurotoxin by mixing together the *botulinum* neurotoxin and the viscous carrier, as well as the product by the this process.

DRAWINGS

The patent or application file contains at least one drawing executed in color. Copies of this patent or patent application publication with color drawing(s) will be provided by the Office upon request and payment of the necessary fee.

In FIG. 1 A is the vastus lateralis (VL) muscle, B is the vastus intermedius muscle (VI), C is the gastrocnemius muscle, and D is the soleus muscle.

Figure 2:
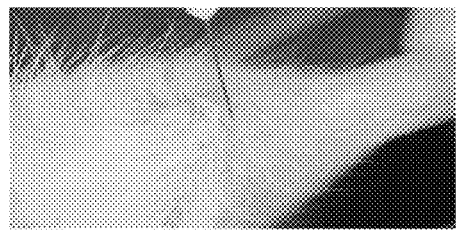
FIG. 2 is a photograph showing an injection of the labeled biologic compound of Example 3 entering the tripennate gastrocnemius lateralis (MGL) portion of the rat gastrocnemius muscle.
Figure 3:
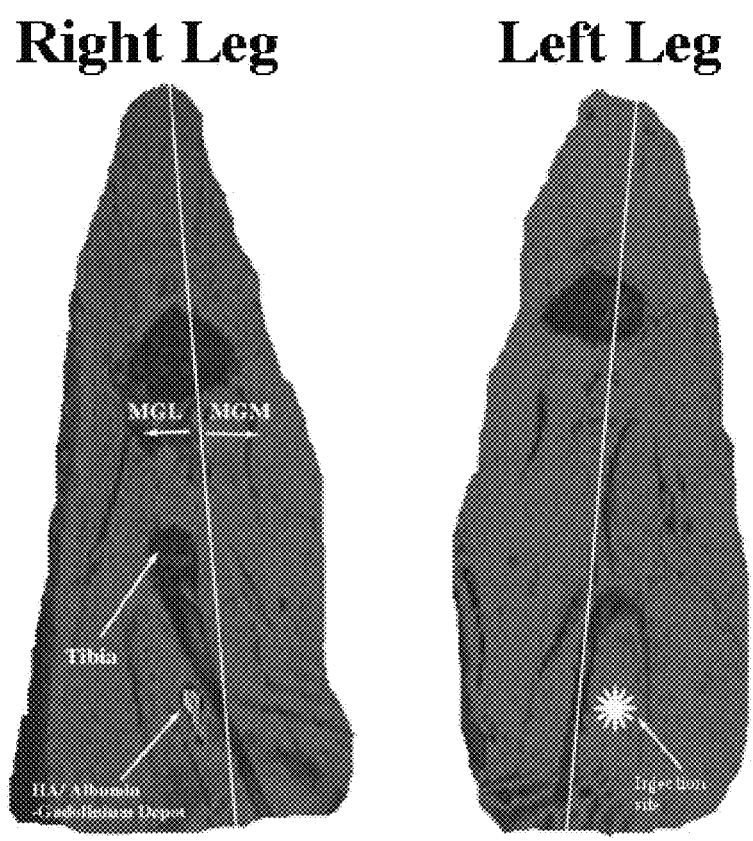

FIG. 3 is a two dimensional magnetic resonance image taken 40 minutes after the FIG. 2 injection oriented longitudinal through the gastrocnemius muscle to show the MGL and unipennate gastrocnemius medialis (MGM) muscle groups in each leg. The right leg was injected with the hyaluronic acid/albumin-gadolinium complex, while the left leg with injected with just the albumin-gadolinium. FIG. 3 shows that the left leg had a diffuse spread of the albumin-gadolinium complex (blue color) throughout the MGL muscle and cross-over to the adjacent MGM muscle, whereas the right leg showed little or no diffusion of the albumin-gadolinium complex (blue color) from the injection site.

DESCRIPTION

The present invention is based on the discovery of a *botulinum* toxin formulation from which the *botulinum* toxin exhibits reduced diffusion from the site of injection, as compared to known aqueous *botulinum* toxin formulations, with without fewer side effects or toxin induced complications.

The *botulinum* toxin formulation we developed comprises a *botulinum* toxin and a polymeric carrier for the *botulinum* toxin. The carrier has the characteristic of high shear thinning so that it is injectable through a 25 to 32 gauge needle.

The carrier in our formulation can be a high molecular weight, polymeric, hyaluronic acid. Hyaluronic acid is a major component of the extracellular matrices of soft tissues, such as the skin and muscle. Low molecular weight (about 1000 Daltons or less) hyaluronic acid can be cleared rapidly from an intradermal or intramuscular location via the lymphatics. A higher molecular weight hyaluronic acid can have a longer tissue residence time and be eliminated from a subdermal site through lower local enzymatic process. We determined that the tissue residency time of a hyaluronic acid in soft tissues can be increased by reducing both lymphatic clearance and that this can be accomplished by increasing the biological stability of the polymer, such as by using particular methods and cross linkers to cross link a low molecular weight hyaluronic acid to thereby prepare a much higher molecular weight (1 million Daltons or higher) hyaluronic acid, which has increased biological stability (meaning that the hyaluronic acid takes longer to biodegrade), is biocompatible and functions as a depot which contains to prevent diffusion of the *botulinum* neurotoxin formulated with the hyaluronic acid in any amounts which exceed the amount of *botulinum* toxin required to saturate adjacent neuromuscular junctions.

We determined that increasing the molecular weight of the polymeric carrier concomitantly increases the local *botulinum* neurotoxin concentration at or near the site of injection. Additionally, we determined that increasing the degree of cross linking of the hyaluronic acid, or increasing the concentration of a hyaluronic acid in the formulation or increasing the molecular weight of the hyaluronic acid used in the formulation results in a longer tissue residence time of the formulation and reduce diffusion of the *botulinum* neurotoxin from the formulation to adjacent muscle groups and importantly also reduces systemic complications form the *botulinum* neurotoxin, as compared to injections of aqueous formulations of the same concentration of the same *botulinum* neurotoxin at the same subdermal injection site.

In our formulation a preferred hyaluronic acid has a molecular weight of from about 10,000 to about 20 million Daltons. A preferred total hyaluronic acid concentration of both crosslinked and uncrosslinked components in our formulation is from about 1 wt % to about 5 wt % cross linked hyaluronic acid. Where a cross linked hyaluronic acid is used the actual crosslinking density (i.e. how many of the hyaluronic acid monomers are actually linked to other hyaluronic acid monomers) is from about 5% to about 40%.

The hyaluronic acid used in our formulations is a natural component of the extracellular matrix of many mammalian tissues therefore providing a biocompatible carrier for the *botulinum* toxin. Additionally, the hyaluronic acid used in our improved formulations increases the viscosity of the formulation, as compared to the viscosity of a *botulinum* toxin formulation which does not comprise any hyaluronic acid, such as BOTOX®, DYSPORT® or MYOBLOC®. Where our formulations have a high viscosity they remain injectable through 25-32 gauge syringe needles because of the high shear rate of the hyaluronic acid used in the formulation.

More important that the specific viscosity of our improved *botulinum* toxin formulation is the depot characteristic of our formulations. Thus, the hyaluronic acid in the formulation act to provide a sustained or modulated release of the *botulinum* toxin so that no or much reduced local and systemic *botulinum* toxin complications occur upon injection of the formulation. It is believed that the hyaluronic acid can act as a tissue adhesive so that when hyaluronic acid is injected into a tissue such as a muscle diffusion and migration of the hyaluronic acid (and hence of the *botulinum* toxin as well) through fascial planes in minimized.

The tissue adhesion and therefore low tissue migration characteristic of our formulations comprising hyaluronic acid enables the formulation including the *botulinum* toxin to remain largely at the injection site. Thus a *botulinum* toxin-hyaluronic acid formulation will have the advantageous characteristic of low diffusion out of the *botulinum* toxin of the peripheral location, such as an intramuscular location (i.e. from an injected the small orbicularis muscle to treat hemifacial spasm). Hence, use of hyaluronic acid in our formulation can limit *botulinum* toxin exposure to surrounding or adjacent non-target tissues, thereby limiting side effects (with regard to para-ocular *botulinum* toxin administration) such as ptosis or visual impairment.

Another advantage of our formulation is that in order to have the *botulinum* toxin released from a carrier solubilized contact with water is required. The preferred hyaluronic acid used provides this through an ability to become hydrated (absorb water).

Additionally, the hyaluronic acid used is a polymer that can be cross-linked to varying degrees, thereby permitting alteration of characteristics such as rate of hyaluronic acid migration for the peripheral location of administration, rate of active agent diffusion and migration out of the hyaluronic acid carrier.

In one embodiment, the present compositions have a viscosity of at least about 10 cps or at least about 100 cps, preferably at least about 1,000 cps, more preferably at least about 10,000 cps and still more preferably at least about 70,000 cps, for example, up to about 250,000 cps, or about 300,000 cps, at a shear rate of 0.1/second. The present compositions are structured or have make-ups so as to be injectable into a peripheral location of a human or animal body preferably through a 27 gauge needle, more preferably through a 29 to 32 gauge needle.

Advantageously, the carrier and therefore our formulation as a viscosity at 25° C. of at least about 10 cps or at least about 100 cps or at least about 1000 cps, more preferably at least about 10,000 cps and still more preferably at least about 70,000 cps or more, for example up to about 200,000 cps or about 250,000 cps, or about 300,000 cps or more, at a shear rate of 0.1/second. The present drug delivery systems not only have the relatively high viscosity as noted above but also have the ability or are structured or made up so as to be effectively placeable, e.g., injectable, into a posterior segment of an eye of a human or animal, preferably through a 27 gauge needle, or even through a 30 gauge needle.

The presently useful carrier preferably is a shear thinning component in that as the present composition containing such a shear thinning carrier is passed or injected into the posterior segment of an eye, for example, through a narrow space, such as 27 gauge needle, under high shear conditions the viscosity of the viscous carrier is substantially reduced during such passage.

Any suitable viscous carrier, for example, ophthalmically acceptable viscous carrier, may be employed in accordance with the present invention. The viscous carrier is present in an amount effective in providing the desired viscosity to the drug delivery system. Advantageously, the viscous carrier is present in an amount in a range of from about 0.5 wt % to about 95 wt % of the drug delivery system. The specific amount of the viscous carrier used depends upon a number of factors including, for example and without limitation, the specific viscous carrier used, the molecular weight of the viscous carrier used, the viscosity desired for the present drug delivery system being produced and/or used and like factors.

Examples of useful viscous carriers include, but are not limited to, hyaluronic acid, carbomers, polyacrylic acid, cellulosic derivatives, polycarbophil, polyvinylpyrrolidone, gelatin, dextrin, polysaccharides, polyacrylamide, polyvinyl alcohol, polyvinyl acetate, derivatives thereof and mixtures thereof.

A dermal filler can also be used as the viscous carrier. Suitable dermal fillers for that purpose include collagen (sterile collagen is sold under the trade names Zyderm, Zyplast, Cosmoderm, Cosmoplast and Autologen), Hylaform® (hyaluronic acid), Restylane® (hyaluronic acid), Sculptra™ (polylactic acid), Radiesse™ (calcium hydroxyl apatite) and Juvederm™ Juvederm™, available from Allergan, Inc. (Irvine, Calif.) comprises a sterile, biodegradable, non-pyrogenic, viscoelastic, clear, colorless, homogenized gel consisting of cross-linked hyaluronic acid formulated at a concentration of 24 mg/ml in a physiologic buffer.

The molecular weight of the presently useful viscous carrier can be in a range of about 10,000 Daltons or less to about 2 million Daltons or more. In one particularly useful embodiment, the molecular weight of the viscous carrier is in a range of about 100,000 Daltons or about 200,000 Daltons to about 1 million Daltons or about 1.5 million Daltons. Again, the molecular weight of the viscous carrier useful in accordance with the present invention, may vary over a substantial range based on the type of viscous carrier employed, and the desired final viscosity of the present drug delivery system in question, as well as, possibly one or more other factors.

In one very useful embodiment, the carrier is a polymeric hyaluronate component, for example, a metal hyaluronate component, preferably selected from alkali metal hyaluronates, alkaline earth metal hyaluronates and mixtures thereof, and still more preferably selected from sodium hyaluronates, and mixtures thereof. The molecular weight of such hyaluronate component preferably is in a range of about 50,000 Daltons or about 100,000 Daltons to about 1.3 million Daltons or about 2 million Daltons. In one embodiment, the present compositions include a polymeric hyaluronate component in an amount in a range about 0.05% to about 0.5% (w/v). In a further useful embodiment, the hyaluronate component is present in an amount in a range of about 1% to about 4% (w/v) of the composition. In this latter case, the very high polymer viscosity forms a gel that slows particle sedimentation rate to the extent that often no resuspension processing is necessary over the estimated shelf life, for example, at least about 2 years, of the drug delivery system. Such a drug delivery system can be marketed in pre-filled syringes since the gel cannot be easily removed by a needle and syringe from a bulk container.

The amount of the *botulinum* neurotoxin selected for local administration to a target tissue according to the present disclosed invention can be varied based upon criteria such as the location of the treatment, or the solubility characteristics of the agent or formulation chosen, as well as the age, sex, weight and health of the patient. For example, the extent of the area of muscle tissue influenced is believed to be proportional to the volume of neurotoxin injected, while the quantity of the relaxation effect is, for most dose ranges, believed to be proportional to the concentration of a Clostridial toxin administered.

Methods for determining the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14$^{th}$ edition, published by McGraw Hill).

According to our invention, the *botulinum* toxin formulation is injected locally (e.g., intramuscular injection) into or in the vicinity of the intended treatment. In some embodiments, the neurotoxin can be administered intradermally and/or subdermally. Further, the formulation can be administered at one or multiple sites.

EXAMPLES

The following examples illustrate aspects of our invention.

Example 1

Low Viscosity *Botulinum* Toxin-Hyaluronic Acid Formulation

A *botulinum* toxin-hyaluronic acid formulation can be prepared as follows. 1 gram of 1,4-butanediol diglycidyl ether (as cross linker) is added to a 1-L aqueous solution containing 10 g hyaluronic acid (as the viscous carrier), adjusted to pH 12 while vortexing. The molecular weight of the uncross linked hyaluronic acid is about 500,000 Daltons. The reaction mixture is incubated at 60° C. for 45 minutes and neutralized with glacial acetic acid. The resulting crosslinked hyaluronic acid can have a crosslinking density of about 10%. Ten milligrams of the crosslinked hyaluronic acid is added to 1 mL of an aqueous solution containing 9 mg sodium chloride, 5 mg human albumin USP and 1,000 mouse $LD_{50}$ units of *botulinum* toxin type A complex. The final solution is lyophilized in a 6-mL type I glass vial. An aliquot of the lyophilized formulation containing 100 mouse LD50 units of toxin and 1 mg of the crosslinked hyaluronic acid is reconstituted with 1 mL of water for injection (WFI) or with saline for injection. The resulting solution has a hyaluronic acid concentration of about 0.1 wt % and a viscosity of about 300 cps.

Example 2

Low Viscosity *Botulinum* Toxin-Hyaluronic Acid Formulation with a Higher Hyaluronic Acid Concentration Another *botulinum* toxin-hyaluronic acid formulation can be prepared as follows. 1 gram of divinyl sulfone (as cross linker) is added to a 500 mL aqueous solution containing 10 g hyaluronic acid (as the viscous carrier) adjusted to pH 14 while vortexing. The molecular weight of the uncross linked hyaluronic acid is about 200,000. The reaction mixture is incubated at 40° C. for 8 hours and neutralized with glacial acetic acid. The resulting crosslinked hyaluronic acid can have a crosslinking density of about 7%. Twenty milligrams of the crosslinked hyaluronic acid is added to 1 mL of an aqueous solution containing 9 mg sodium chloride, 5 mg human albumin USP and 1,000 mouse $LD_{50}$ units of *botulinum* toxin type A complex. The final solution is lyophilized in a 6-mL type I glass vial. An aliquot of the lyophilized formulation containing 100 mouse LD50 units of toxin and 1 mg the crosslinked hyaluronic acid is reconstituted with 1 mL of water for injection (WFI) or with saline for injection. The resulting solution has a hyaluronic acid concentration of about 0.5 wt % and a viscosity of about 300 cps. Since the amount of cross linking is decreased in the Example 2 formulation the concentration of the hyaluronic acid in the formulation is increased to provide the same viscosity as the Example 1 formulation Example 3

High Viscosity *Botulinum* Toxin-Hyaluronic Acid Formulation

A high viscosity *botulinum* toxin-hyaluronic acid formulation can have the ingredients shown in Table 1 below.

TABLE 1

| Ingredient | Amount |
| --- | --- |
| Botulinum toxin type A | 100 units |
| Sodium hyaluronate (polymeric) | 2.5% (w/v) |
| Sodium chloride | 0.63% (w/v) |
| dibasic sodium phosphate, heptahydrate | 0.30% (w/v) |
| Monobasic sodium phosphate, monohydrate | 0.04% (w/v) |
| Water for Injection | q.s. |

TABLE 1-continued

| Ingredient | Amount |
| --- | --- |
| Viscosity at shear rate 0.1/second at 25° C. | 170,000 ± 25% cps |

Preferably the *botulinum* toxin used is BOTOX®, which is a lyophilized, powdered form of a *botulinum* toxin type A stabilized with albumin and sodium chloride. The formulation is made by first reconstituting the powdered *botulinum* toxin with isotonic saline (sodium chloride) (thereby making part 1). The sodium hyaluronate can be purchased as a sterile powder or sterilized by filtering a dilute solution followed by lyophylization of the sodium hyaluronate to yield a sterile sodium hyaluronate powder. The sterile sodium hyaluronate is dissolved in water to make an aqueous concentrate (thereby making part 2). Part 1 and part 2 are then mixed together to provide the ingredient concentrations shown in Table 1. Thus, the reconstituted *botulinum* toxin is mixed with the sodium hyaluronate concentrate to form a gel, and the phosphate buffers are then added. Water is added q.s. (quantum sufficit, as much as suffices, in this case as much as is required to prepare the homogenous mixture, dispersion, gel or suspension) and the mixture is mixed until homogenous. The formulation so prepared (or an aliquot thereof) can be locally injected using a 27 gauge or a 30 gauge needle to provide a desired therapeutic or cosmetic effect.

The sodium hyaluronate powders used in the formulation has a water contents in a range of about 4% to about 20%, preferably about 4% to about 8%, by weight. Because the formulation has a density of about 1 gm/ml, the percentages set forth herein as being based on weight per volume (w/v) can also be considered as being based on weight per weight (w/w).

The formulation of Examples 3 uses a sufficient concentration of high molecular weight, sodium hyaluronate so as to form a gelatinous plug or drug depot upon local, subdermal injection of the formulation. Preferably the average molecular weight of the hyaluronate used is less than about 2 million, and more preferably the average molecular weight of the hyaluronate used is between about 1.3 million and 1.6 million. Since sodium hyaluronate solutions comprised of high molecular weight hyaluronic acid are subject to dramatic shear thinning, these formulations are easily injected through 27 gauge or even 30 gauge needles. Low molecular weight and cross-linked hyaluronic acids exhibit little if any shear thinning and can be useful to prepare formulations within the scope of our invention, as low viscosity formulations.

The most preferred viscosity range for the formulation is 140,000 cps to 280,000 cps at a shear rate 0.1/second at 25° C.

The formulation is formulated using excipients that are fully biocompatible (i.e. non-toxic) and is buffered at physiological pH by the low concentration of sodium phosphate salts; rendered isotonic with sodium chloride, and use Water for Injection, USP.

Example 4

In Vivo Diffusion of Biologic-Hyaluronic Acid Formulations

We developed an animal model to assess in vivo subdermal residency time of a biologic-hyaluronic acid formulation. *Botulinum* toxin is a biologic. Using this model we were able to examine localization of the biologic-hyaluronic acid formulation in a specific muscle and the ability of the polymeric formulation containing a crosslinked hyaluronic acid to increase the residency time of the biologic in the muscle. In this Example we used albumin as a surrogate for *botulinum* toxin in the hyaluronic acid formulation prepared.

Figure 1:
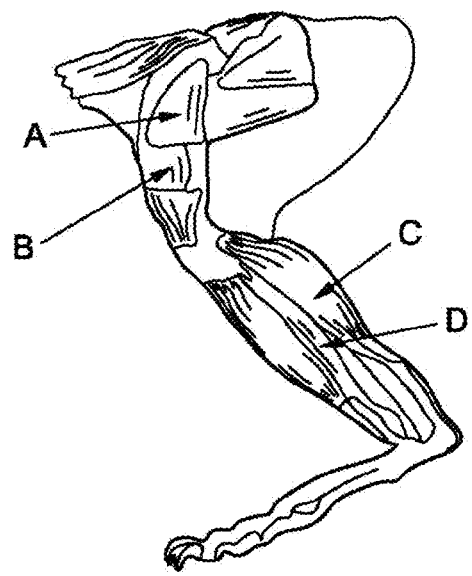
FIG. 1 is a schematic drawing showing the rat hind leg muscles.

The rat gastrocnemius muscle consists of two distinct muscles, the tripennate gastrocnemius lateralis (MGL) and the unipennate gastrocnemius medialis (MGM)(see FIG. 1). We examined the movement of a biologic compound injected into the MGL and quantified the amount identified in the adjacent MGM muscle using high resolution dynamic MRI. The biologic compound was a Albumin-Gadolinium complex with a molecular weight of about 65,000 Daltons (obtained from Biopal, Worcester, Mass.) and the injection site was in the MGL muscle, with the needle placed 2 cm from the heel, lateral to the tibia with an injection depth of 4 to 5 mm (see FIG. 2).

A polymeric formulation using crosslinked hyaluronic acid was made using the Albumin-Gadolinium complex which had a final concentration of $2 \times 10^{-4}$ M in the formulation. The crosslinked hyaluronic acid used was Juvederm™ (Allergan, Irvine, Calif.). Juvederm™ is a sterile, biodegradable, non-pyrogenic, viscoelastic, clear, colorless, homogenized gel consisting of cross-linked hyaluronic acid formulated at a concentration of 24 mg/ml in a physiologic buffer.

A 5 microliter injection of the hyaluronic acid-Albumin-Gadolinium complex was performed in the MGL muscle of the right leg, and the left leg had a similar injection of the same formulation without the hyaluronic acid. The primary outcome measure was the amount of Albumin-Gadolinium that diffused to the MGM muscle in each leg.

Results from this experiment showed that there was rapid spread of the Albumin-Gadolinium complex in the left calf with cross-over to the MGM muscle within the first hour (see FIG. 3). In the right leg, the injected hyaluronic acid-Albumin-Gadolinium complex stayed primarily within the injected depot area in the MGL muscle and there was minimal signal present in the adjacent MGM muscle. These results indicate that a hyaluronic acid based formulation can be used limit the diffusion of a biologic compound (such as a *botulinum* toxin) from the injected muscle site.

Example 5

*Botulinum* Toxin-Hyaluronic Acid Formulation for Treating Cervical Dystonia

A male patient age 45 suffering from A male suffering from cervical dystonia as manifested by spasmodic or tonic contractions of the neck musculature, producing stereotyped abnormal deviations of the head, the chin being rotated to one side, and the shoulder being elevated toward the side at which the head is rotated, is treated by injection of the Example 1 formulation comprising about 75-125 units of the *botulinum* toxin type A. Within 3-7 days, the symptoms are substantially alleviated, that is the patient is able to hold his head and shoulder in a normal position.

EMG recording indicates no local diffusion of the *botulinum* toxin out of the injected muscle area is detected as no paralysis of adjacent muscles occurs. No diffusion of the *botulinum* neurotoxin into deep neck muscles is indicated as no weakness of the pharyngeal and esophageal muscles results and the patient has no difficulty swallowing (dysphagia) at any time after the injection. Nor does any dysarthria occur.

Example 6

Botulinum Toxin-Hyaluronic Acid Formulation for Treating Blepharospasm

The Example 2 formulation comprising about 1-5 units of the botulinum toxin per muscle is intramuscularly injected into a patient to treat his blepharospasm. The formulation is injected into the lateral pre-tarsal orbicularis oculi muscle of the upper lid and the lateral pre-tarsal orbicularis oculi of the lower lid.

No diffusion of the botulinum neurotoxin into the deeper levator muscle is observed. Additionally the patient does not experience any ptosis or brow ptosis or visual field impairment. EMG recording indicates no diffusion of the botulinum toxin out of the orbicularis muscle into the frontalis muscle, the deeper rectus muscles or into the zygomaticus major muscle. Notably, the patient does not experience any medial ectropion, chronic tearing, double vision or asymmetric facial expression.

Example 7

Botulinum Toxin-Hyaluronic Acid Formulation for Treating Strabismus

The Example 3 formulation comprising about 1-5 units of BOTOX® is used to treat strabismus by local injection of the extraocular (medial rectus) muscles of a patient with strabismus. The number of units of the botulinum toxin injected can vary based upon both the size of the muscle to be injected and the extent of muscle paralysis desired (i.e. amount of diopter correction desired).

The patent experiences no esotropia, nor any double vision. Unaltered EMG (electromyographic) recording shows that no botulinum toxin has diffused into the muscle cone and that the other recti leading has not been paralyzed.

Example 8

Botulinum Toxin-Hyaluronic Acid Formulation for Treating Headache

A patient with migraine is pericranially injected (injected symmetrically into glabellar, frontalis and temporalis muscles) with sufficient Example 1, 2 or 3 formulation to comprise an injection of 25 U of the botulinum toxin. The patient shows significant benefit as the migraine subsides within a day or two. EMG recording shows that no botulinum toxin has diffused from the injected muscles.

Example 9

Botulinum Toxin-Hyaluronic Acid Formulation for Cosmetic Use

A patient with prominent glabellar lines is injected with sufficient Example 1, 2 or 3 formulation to comprise an injection of about 30 units of the botulinum toxin. The formulation is injected intramuscularly with 10 units into the procerus muscle and 10 units injected intramuscularly into each corrugator supercilii muscle).

No diffusion of the botulinum neurotoxin into non-injected muscle is observed, using EMG. The patient does not experience any ptosis or brow ptosis or any asymmetric facial expression.

Advantages of our formulations include increasing residency of the botulinum neurotoxin will increase the efficiency of deactivating nerve terminals in a given muscle and potentially increase the duration of the muscle paralysis. Additionally, increasing the residency time of the botulinum neurotoxin in the muscle tissue can also reduce exposure of the botulinum neurotoxin to the lymphatic system. It is know that antibody production to an antigen requires drainage of the antigen to regional lymph nodes thereby exposing the antigen to the immune system. Antibodies to the antigen are produced, and in the case of a biologic, such as a botulinum toxin, neutralizing antibodies can form which may be one factor leading to 'neurotoxin resistance' and poor therapeutic responses following injection. A botulinum neurotoxin is not stable long-term in muscle tissue and require an acidic environment, preferably in the pH range around 5, to prevent degradation. Therefore, increasing tissue residency times, will allow for local degradation of the botulinum neurotoxin so that the lymphatic systems does not have exposure to the parent species and neutralizing antibodies may not be produced.

All references, articles, patents, applications and publications set forth above are incorporated herein by reference in their entireties.

Accordingly, the spirit and scope of the following claims should not be limited to the descriptions of the preferred embodiments set forth above.

We claim:

1. A method for treating a disease or condition in a human patient by administering to the patient a pharmaceutical composition comprising a botulinum neurotoxin, albumin and a viscous carrier for the botulinum neurotoxin, wherein the viscous carrier comprises a cross-linked hyaluronic acid having a molecular weight ranging from about 10,000 daltons to about 200,000 daltons, a crosslinking density ranging from about 5% to about 10%, present in a range from about 1% to about 4% (w/v) of the pharmaceutical composition, wherein the pharmaceutical composition having a viscosity range from about 100 cps to about 1,000 cps at a shear rate 0.1/second at 25° C.; and wherein the patient experiences significantly fewer complications due to the botulinum toxin than occur upon administration of a botulinum toxin containing pharmaceutical composition which does not comprise a viscous carrier.

2. The method of claim 1, wherein the administering is carried out by local subdermal injection of the pharmaceutical composition.

3. The method of claim 1, wherein the disease or condition is selected from the group of diseases and conditions consisting of dystonia, cervical dystonia, blepharospasm, strabismus, spasticity, movement disorder, headache, migraine, hyperhydrosis, overactive bladder, prostate disorder, articular pathology, arthritis, facial wrinkles, and glabellar lines.

4. The method of claim 1, wherein the complications are local complications selected from the group of local complications consisting of ptosis, brow ptosis, visual field impairment, double vision, ectropion, tearing, asymmetric facial expression, dysphagia, and muscle weakness.

5. The method of claim 1, wherein the complications are systemic complications selected from the group of system complications consisting of respiratory distress, generalized weakness, dry mouth, nausea, headache, constipation and vertigo.

6. The method of claim 1, wherein the patient experiences no complications during any ten day period up to six months after the administration.

7. The method of claim 1, wherein the viscous carrier further comprises uncrosslinked hyaluronic acid.

* * * * *